(12) United States Patent
Thompson et al.

(10) Patent No.: US 11,980,562 B2
(45) Date of Patent: May 14, 2024

(54) RECONFIGURABLE ORTHOSIS FOR DEFORMITY CORRECTION

(71) Applicant: Green Sun Medical, LLC, Fort Collins, CO (US)

(72) Inventors: Matthew Thompson, Corte Madera, CA (US); Darin Gittings, Sunnyvale, CA (US)

(73) Assignee: Green Sun Medical, LLC, Fort Collins, CO (US)

( * ) Notice: Subject to any disclaimer, the term of this patent is extended or adjusted under 35 U.S.C. 154(b) by 51 days.

(21) Appl. No.: 16/161,447

(22) Filed: Oct. 16, 2018

(65) Prior Publication Data
US 2019/0183668 A1 Jun. 20, 2019

Related U.S. Application Data

(60) Provisional application No. 62/598,657, filed on Dec. 14, 2017.

(51) Int. Cl.
*A61F 5/00* (2006.01)
*A61F 5/02* (2006.01)
(Continued)

(52) U.S. Cl.
CPC ............... *A61F 5/02* (2013.01); *A61F 5/024* (2013.01); *A61F 5/26* (2013.01); *A61F 2005/0197* (2013.01)

(58) Field of Classification Search
CPC .... A61F 5/024; A61F 5/02; A61F 5/01; A61F 5/055; A61F 5/028; A61F 5/026;
(Continued)

(56) References Cited

U.S. PATENT DOCUMENTS 757,140 A * 4/1904 Neffeler ................. A61F 5/028
602/19
970,781 A 9/1910 Joseph
(Continued)

FOREIGN PATENT DOCUMENTS

CN 1349395 A 5/2002
CN 200963211 Y 10/2007
(Continued)

OTHER PUBLICATIONS

International Preliminary Report on Patentability for PCT/US2018/06556 dated Jun. 16, 2020.
(Continued)

*Primary Examiner* — Adam Baker
(74) *Attorney, Agent, or Firm* — Wilson Sonsini Goodrich & Rosati

(57) ABSTRACT

Systems and methods for correcting spinal deformity utilize a dynamic, multi-structure torso orthosis that allows motion during wear. The disclosed embodiments utilize a series of elastically coupled ring structures that conform to the circumference of the torso of a patient. Adjustable elastic coupling mechanisms are utilized to create and alter forces and moments that are applied to the torso through these ring structures. In some instances, the ring structures are formed from individual elements that can be linked to accommodate particular anatomies. In other instances, a superior ring structure can be configured to accommodate the patient's upper torso.

23 Claims, 18 Drawing Sheets

(51) Int. Cl.
*A61F 5/26* (2006.01)
*A61F 5/01* (2006.01)

(58) Field of Classification Search
CPC ...... A61F 5/03; A61F 5/00; A61F 5/28; A61F 5/0102; A61F 5/30; A61F 5/32; A61F 13/14; A61H 1/0292; A61H 1/0218; A61H 1/008; A61B 17/62; A61B 17/82; A41F 9/02; A41F 9/025
USPC .......................................................... 602/19
See application file for complete search history.

(56) References Cited

U.S. PATENT DOCUMENTS

| | | | |
|---|---|---|---|
| 1,589,670 A | 6/1926 | Vartia | |
| 1,650,650 A | 11/1927 | Pieper | |
| 2,223,276 A | 11/1940 | Ward | |
| 2,687,129 A | 8/1954 | Talkish | |
| 2,835,247 A | 5/1958 | Stabholc | |
| 3,177,869 A | 4/1965 | Bartels | |
| 3,420,230 A | 1/1969 | Louis | |
| 3,926,182 A | 12/1975 | Stabholz | |
| 3,945,376 A | 3/1976 | Kuehnegger | |
| 4,230,101 A | 10/1980 | Gold | |
| 4,648,390 A * | 3/1987 | Friddle | A61F 5/024 602/19 |
| 4,807,605 A | 2/1989 | Mattingly | |
| 5,012,798 A | 5/1991 | Graf et al. | |
| 5,103,811 A | 4/1992 | Crupi, Jr. | |
| 5,127,897 A | 7/1992 | Roller | |
| 5,405,313 A | 4/1995 | Albin | |
| 5,449,338 A | 9/1995 | Trudell | |
| 5,503,621 A | 4/1996 | Miller | |
| 5,586,561 A * | 12/1996 | Archer, III | A41D 13/0153 128/846 |
| 5,840,051 A | 11/1998 | Towsley | |
| 5,876,361 A | 3/1999 | Harris et al. | |
| 5,916,188 A | 6/1999 | Ousdal | |
| 6,280,405 B1 | 8/2001 | Broselid | |
| 6,319,216 B1 * | 11/2001 | Coligado | A61F 5/028 602/5 |
| 6,605,052 B1 | 8/2003 | Cool et al. | |
| 6,676,617 B1 | 1/2004 | Miller | |
| 6,749,579 B1 | 6/2004 | Schroder | |
| 7,654,973 B2 | 2/2010 | Firsov | |
| 7,766,850 B2 | 8/2010 | Simanovsky | |
| 7,967,767 B2 | 6/2011 | Ogilvie | |
| 8,066,653 B2 | 11/2011 | Seon | |
| 8,235,924 B2 | 8/2012 | Bachmann et al. | |
| 9,452,074 B2 | 9/2016 | Wynne et al. | |
| 9,522,077 B1 | 12/2016 | Johnson | |
| 9,572,705 B2 | 2/2017 | Ingimundarson et al. | |
| 10,667,940 B2 * | 6/2020 | Thompson | A61F 5/02 |
| 2004/0073150 A1 | 4/2004 | Roballey | |
| 2005/0010150 A1 | 1/2005 | Firsov | |
| 2005/0043660 A1 | 2/2005 | Stark et al. | |
| 2005/0137510 A1 | 6/2005 | Dauny | |
| 2006/0287625 A1 | 12/2006 | Rauch | |
| 2007/0010768 A1 | 1/2007 | Simanovsky | |
| 2008/0021357 A1 * | 1/2008 | Firsov | A61F 5/026 602/19 |
| 2008/0208089 A1 | 8/2008 | Newkirk | |
| 2008/0262402 A1 | 10/2008 | Ogilvie | |
| 2009/0054818 A1 | 2/2009 | Kaufman et al. | |
| 2011/0184325 A1 | 7/2011 | Behzadian et al. | |
| 2011/0295170 A1 | 12/2011 | Laranjeira et al. | |
| 2012/0157901 A1 | 6/2012 | Galante | |
| 2014/0012171 A1 | 1/2014 | Brown et al. | |
| 2015/0297387 A1 | 10/2015 | Thompson et al. | |
| 2015/0328035 A1 | 11/2015 | Idowu et al. | |
| 2016/0008206 A1 | 1/2016 | Devanaboyina | |
| 2017/0042717 A1 | 2/2017 | Agrawal et al. | |
| 2017/0196722 A1 | 7/2017 | Murdock | |
| 2018/0028345 A1 * | 2/2018 | Karasahin | A61F 5/0102 |
| 2019/0262160 A1 | 8/2019 | Thompson et al. | |

FOREIGN PATENT DOCUMENTS

| | | |
|---|---|---|
| CN | 201337539 Y | 11/2009 |
| CN | 201930103 U | 8/2011 |
| CN | 102599999 A | 7/2012 |
| CN | 205696114 U | 11/2016 |
| CN | 107110485 A | 8/2017 |
| DE | 2743996 A1 | 4/1979 |
| EP | 1854435 A2 | 11/2007 |
| EP | 1983947 A1 | 10/2008 |
| ES | 2065289 A1 | 2/1995 |
| ES | 2264590 A1 | 1/2007 |
| FR | 2404430 A1 | 4/1979 |
| FR | 2591473 A1 | 6/1987 |
| GB | 190221246 A | 9/1903 |
| GB | 203975 A | 9/1923 |
| GB | 2215607 A | 9/1989 |
| JP | 2005137448 A | 6/2005 |
| JP | 2005349177 A | 12/2005 |
| JP | 2009119276 A | 6/2009 |
| JP | 2009148403 A | 7/2009 |
| KR | 20040103300 A | 12/2004 |
| KR | 20040103301 A | 12/2004 |
| RU | 2119312 C1 | 9/1998 |
| RU | 2131713 C1 | 6/1999 |
| TW | M280687 U | 11/2005 |
| WO | WO-02100304 A1 | 12/2002 |
| WO | WO-2005105004 A1 | 11/2005 |
| WO | WO-2012120316 A2 | 9/2012 |
| WO | WO-2015109174 A1 | 7/2015 |
| WO | WO-2019118789 A1 | 6/2019 |

OTHER PUBLICATIONS

Office action dated Feb. 6, 2020 for U.S. Appl. No. 16/406,999.
Office action dated Jun. 21, 2018 for U.S. Appl. No. 14/598,543.
Office action dated Jul. 29, 2019 for U.S. Appl. No. 16/406,999.
Office action dated Aug. 6, 2019 for U.S. Appl. No. 14/598,543.
EP15736949 Extended European Search Report dated Feb. 12, 2018.
International Search Report and Written Opinion dated Apr. 8, 2015 for International PCT Patent Application No. PCT/US2015/011741.
Office Action dated Jul. 7, 2017 for U.S. Appl. No. 14/598,543.
Office Action dated Dec. 8, 2016 for U.S. Appl. No. 14/598,543.
Final Office action dated Dec. 13, 2018 for U.S. Appl. No. 14/598,543.
U.S. Appl. No. 16/406,999 Office Action dated Feb. 14, 2022.
EP18888573.5 Extended Search Report dated Aug. 9, 2021.
U.S. Appl. No. 14/598,543 Notice of Allowance dated Jan. 28, 2020.
U.S. Appl. No. 16/406,999 Office Action dated Nov. 5, 2020.

* cited by examiner

RECONFIGURABLE ORTHOSIS FOR DEFORMITY CORRECTION

CROSS REFERENCE TO RELATED APPLICATION

This application claims the benefit of provisional application 62/598,657, filed Dec. 14, 2017, the full disclosure of which is incorporated herein by reference.

BACKGROUND OF THE INVENTION

Adolescent Idiopathic Scoliosis (AIS) is an unnatural curvature of the spine that affects 2-3% of the population. Onset of this disease is typically around 10 years of age and is commonly detected (in the United States) in school screenings. The severity of the deformity is measured with the Cobb angle, the inside angle formed by the two most tilted vertebrae. The minimum Cobb angle for a diagnosis of IAS is 10 degrees. While many think of scoliosis as a curvature in the coronal plane, scoliosis can be a complex three-dimensional deformity often involving sagittal curves and rotational deformity in the axial plane.

The natural history of the disease is that many children will have curves of 10-20 degrees that remain static. Such an amount of curvature rarely requires treatment. The remainder of children with scoliosis have curves that continue to progress. Once the patient hits skeletal maturity, their curve will cease to progress if the Cobb angle measures less than 40 degrees. Curves with a Cobb angle of 40 degrees and greater, typically continue to progress.

Treatment for scoliosis is typically observational when curves are less than 25 degrees. Once curves reach 25 to 30 degrees of Cobb angle the patient is braced in an attempt to slow or halt progression of the curve. Curves that progress to 40 degrees or more are treated surgically with a spinal fusion.

Clinical studies have discovered two requirements for success in brace treatment: brace wear for 20 hours a day or more and acute correction of the scoliotic curve of at least 50% at brace application.

The current state of the art (standard of care) in bracing is a rigid full-torso brace known as a thoracolumbar-sacral orthosis (TLSO). This is typically a thermoplastic shell that is custom molded to the patient's torso with modifications that are intended to reduce the curvature through contact forces. These braces may have some effect in halting the progression of the curvature when worn comprehensively (often more than 20 hours per day) through the treatment period. Often these patients will be prescribed a brace for four or more years.

A significant improvement over the current state-of-the-art is described in commonly owned U.S. Patent Publication 2015/0297387, the full disclosure of which is incorporated herein by reference. That publication describes systems for externally applying corrective force to a vertebral column of a patient. As illustrated in FIG. 1, the systems of the '387 publication include plurality of ring segments that are each adapted to conform to the circumference of the torso of a patient where the ring structures are positioned in a vertically spaced, substantially coaxial configuration. The ring structures include an inferior terminal ring structure, a superior terminal ring structure, and at least one intermediate ring structure disposed between the inferior terminal ring structures. Drive unit are disposed on all but the superior ring structure, and receivers are disposed on all but the inferior ring structure. The drive units and receivers are disposed on at least the dorsal regions of the ring structures, and usually on at least some of the lateral regions as well. An elastic member extends from each drive unit to the vertically adjacent receiver, and the drive unit is configured to apply a rotational force to an end of the elastic member to deflect an axis of the elastic member to apply a force in a lateral plane on the receiver on an adjacent ring structure. Dorsally located drive units and receivers will apply a force to the torso in an anterior-posterior (dorsal-ventral) direction, while laterally located drive units and receivers will apply a force in a lateral-medial direction.

While the improved designs of the '387 publication are very effective, certain design aspects of the described systems could be improved. For example, the ring structures described in the '387 publication are difficult to reconfigure to accommodate different anatomies. Additionally, the ring structures are somewhat flexible can reduce the restorative force applied from the drive units to the spine. Still further, the superior ring structure is limited in how far it can extend up the patient's back and chest, thus reducing force that can be applied to the upper torso.

For these reasons, it would be desirable to provide improved systems for externally applying corrective force to a torso and in particular to a vertebral column of a patient. In particular, such improved systems should be adjustable to conform to different patient anatomies, should have sufficient rigidity to effectively apply force to the patient's spine, and should be able to engage and apply forces to the patient's torso over regions above the arms. At least some of these objectives will be met by the inventions described and claimed herein.

SUMMARY OF THE INVENTION

In a first aspect, the present invention provides a system for externally applying corrective forces to a torso of a patient, for example for the purpose of treating scoliosis and other spinal deformities. The systems comprises a plurality of ring structures attached together and spaced-apart along a vertical axis, typically including at least an inferior terminal ring structure, a superior terminal ring structure, and one or more intermediate ring structures disposed between the inferior and superior terminal ring structures. At least some of the ring structures will comprise a plurality of discrete or individual elements linked together so that said ring structure can be assembled from selected individual elements to conform to the circumference of the torso of the patient at a particular level, typically at or between the hip and the shoulders. In at least most instances, the individual ring elements will have complimentary shapes and mating surfaces so that they are interchangeable. At least some of the interchangeable ring elements will have different geometries and/or sizes, such as different degrees of bending and/or different lengths so that when assembled the overall geometry of the ring structure may vary in shape, size, and typically both shape and size.

While most of the individual ring elements will be solid and be configured to attach rigidly in tandem to other solid elements to form a generally rigid assembly, some of the individual ring elements may have other characteristics or features. For example, some of the individual ring elements may be hinged in the middle so that once the individual ring elements are assembled and generally rigid in structure, the ring structure itself may still be opened and closed at the hinge so that it may be placed over and removed from the patient.

The plurality of ring structures will usually be vertically joined by coupling members. Typically, at least one coupling member will be disposed between each vertically adjacent pair of ring structures. The coupling members will be attached at an inferior end to the inferior ring and at a superior end to the superior ring, and will usually be configured to apply a horizontal displacement force between vertically adjacent ring structures in order to treat the scoliosis or other patient condition. In addition to these force-applying coupling members, the vertically adjacent ring structures will usually also be joined by another external structure which supports the rings and locates each rings at its proper level on the patient's torso. As described in more detail below, the external structure can be a soft cover or vest which receives the rings, can be a combination of shoulder straps attached to the superior ring and additional straps or other suspension members between each pair of rings below the superior rings, or could be a variety of other structures or assemblies. Suitable suspension members between vertically adjacent ring structures include flexible straps, rigid struts, woven nets, low-profile springs, and the like. The suspension members may be elastic, rigid, and combinations thereof, and suspension members having different characteristics may be employed in combination on a single orthosis.

The individual ring elements may be circumferentially joined in a variety of ways. Typically, they will be fixedly attached to each other, for example, by screws or other fasteners. Alternatively, they could be joined by pins, straps, clamps, or other removable fixation elements. Typically, the ring structures will include hinged or other elements which allow them to be opened sufficiently to be placed around the torso of the patient and to then be closed to provide a relatively rigid circumscribing structure around the patient. Often, a gap will be left in the ring structure, typically on the anterior side, so that the ring can be closed and cinched using a closure element, such as strap or other removable gap closure device.

At least some of the coupling members disposed between vertically adjacent pairs of ring structure will typically be located on a dorsal side of the ring structures. The coupling members on the dorsal side of the ring structure will typically include a pair of spring members configured to apply forces in the anterior-posterior direction in order to provide corrective forces. Often, the pair of spring members in a particular coupling member will apply forces in opposite directions to impart a rotational displacement force between the upper and lower rings. Additionally, coupling members will often be provided on the lateral sides of the ring structures in order to provide restorative forces in a lateral direction. Often the lateral coupling members will include only a single spring member.

The ring structures may be planar, that is the entire ring element may have a periphery lying in a single plane. In other instances, the ring structures may have portions of their periphery lying in vertically spaced apart planes. In such cases, at least some of the individual ring elements will typically extend vertically to provide the desired the planar separation.

In a second aspect, the present invention provides a system for externally applying forces to a torso of a patient for correcting spinal or other deformities. The system includes a plurality of ring structures that are configured to conform to a circumference of the patient at different levels along the torso of the patient where the ring structures are each positioned in a vertically spaced, substantially co-axial configuration about a vertical (superior-inferior) axis of the patient. The plurality of ring structures includes at least an interior terminal ring structure, a superior terminal ring structure, and one or more intermediate ring structures disposed between the inferior and superior ring structures. In this aspect of the invention, the superior ring structure is configured to have at least a posterior region which spans an upper region of the patient's back at or above the patient's arms and opposed lateral regions which are displaced downwardly from the posterior region to extend below the patient's arms. An anterior portion of such superior rings may extend across the patient's torso at a level above or below the arms, usually being configured to avoid a female patient's breasts. Such superior ring structures have been found to be particularly effective in applying force to the upper regions of the torso and the spine. Usually, the intermediate and inferior ring structures will have flat or planar configurations free from vertical displacements. As with earlier embodiments, coupling members are disposed between vertically adjacent pairs of ring structures to provide a desired restorative force to the rings.

In particular embodiments, the anterior and posterior portions of the superior rings may be at the same level to span the patient's anterior and posterior torso above the patient's arms, with a well or U-shaped depression formed in the lateral portions of the superior ring for accommodating the patient's arms. The superior and other ring structures in these embodiments are preferably formed from a plurality of individual ring elements as described previously with the earlier embodiments herein.

In a third aspect of the present invention, a method for configuring a system to apply a corrective force to a torso of a patient to treat spinal or other deformities comprises providing a plurality of individual ring elements and linking selected ones of the individual ring elements together to form an inferior terminal ring structure, a superior terminal ring structure, and at least one intermediate ring structure disposed between the inferior and superior ring structures. The individual ring elements will be assembled so that each ring structure has a geometry which conforms to a circumference of the patient's torso at the vertical level where the ring structure will reside. After the individual ring structures are assembled, they will be elastically joined in a vertical stack to provide three or more levels of ring structures in order to treat the patient.

Usually, at least some of the individual ring elements will have different geometries from others of the individual ring element, typically having at least one of a different degree of curvature and a different length. In this way, ring structures have a variety of geometries, shapes, and sizes can be configured from the same inventory or kit of individual ring elements. The individual ring elements will often be provided or maintained as kits, inventories, or other collections available to a user for assembly into the ring structures and orthoses of the present invention. Such collections will usually include ring elements having at least two different geometries (i.e. differing in size and/or shape), more usually having at least three different geometries, and often having at least four, five, six, seven, eight, or more different geometries.

Elastically joining the different levels of ring structures will typically comprise placing at least one coupling member, typically an elastic coupling member, between each vertically adjacent pair of ring structures. Typically including at least one elastic member on the posterior surfaces of the ring structures and often at least one elastic member on the lateral aspects of the ring members.

In a fourth aspect of the present invention, a system for externally applying corrective force to a torso of a patient comprises a plurality of ring structures spaced-apart along a vertical axis, where the plurality of ring structures includes an inferior terminal ring structure, a superior terminal ring structure, and at least one intermediate ring structure disposed between the inferior and superior terminal ring structures. At least one coupling member will be disposed between each vertically adjacent pair of ring structures, and each coupling member will typically be secured at an inferior end to the inferior ring structure and at a superior end to the superior ring structure. As with all earlier embodiments, at least some of the coupling members are configured to apply horizontal displacement forces between the vertically adjacent rings in order to achieve a desired restorative force. The assembly of the vertically spaced-apart ring structures will be secured to the patient by a harness which is attached to the superior ring structure which is configured to the vertically adjustable to position the ring structures properly relative to the patient's posterior anatomy. In addition to the harness which suspends the superior ring structure, the support systems will preferably include a plurality of vertical suspension straps placed between each of the vertically adjacent pairs of rings. In this way, the position of the rings on the patient's torso will be maintained by the harness and the vertical suspension straps so that the rings will not be displaced by patient movements. A suspension system will be provided in addition to the coupling members which are disposed between the adjacent vertical rings. The purpose of the coupling members is to apply a displacement force in a horizontal direction, not to vertically support the ring structures while being worn by a patient. Such support function is provided by the separate suspension system.

In a fifth aspect of the present invention, a system for externally applying corrective force to the torso of a patient comprises a plurality of ring structures including an inferior terminal ring structure, a superior terminal ring structure, and at least one intermediate main structure disposed between the inferior and superior terminal ring structures. At least one coupling member will be disposed between each vertically adjacent pair of ring structures and each coupling member will be secured at an inferior end to the inferior ring structure and at a superior end to the superior ring structure. The coupling members are configured to apply horizontal displacement forces between the vertically adjacent rings. In this aspect of the present invention, a posterior bar having right and left lateral ends is positioned vertically above the superior ring structure. At least one superior coupling members is disposed between the superior ring structure and the posterior bar such that the superior coupling members secured at an inferior end to the superior ring structure in that a superior end to the posterior bar and the superior coupling member is configured to apply horizontal displacement forces between the superior ring structure and the posterior bar. By attaching a strap to at least one of the two lateral ends of the posterior bar, a shoulder of the patient can be circumscribed with the strap and the shoulder displaced by forces applied by the posterior bar, where the forces are transmitted from the superior ring structure.

In a sixth aspect of the present invention, a system for externally applying corrective forces to a torso of a patient comprises a plurality of ring structures spaced-apart along the vertical axis. The plurality of ring structures includes an inferior terminal ring structure, a superior terminal ring structure, and at least one intermediate ring structure disposed between the superior and inferior ring structures. At least one coupling member is disposed between each vertically adjacent pair of ring structures, and the coupling members comprise (a) an axially extendable (telescoping) leaf spring having a superior end and an inferior end, (b) a horizontal biasing member pivotably secured between the inferior ring structure and the inferior end of the axially extendable leaf spring, and (c) a universal joint secured between the superior end of the axially extendable leaf spring and the superior ring structure. Such coupling members are unconstrained relative to vertical and horizontal displacement of the adjacent ring structures but are configured to apply a force in a direction normal to a plane of leaf spring to apply a desired corrective force to the torso. That is, for posterior coupling members and drive units will apply an inward or outward force in an anterior-posterior direction. For lateral coupling members and drive units, the force will be in a lateral-medial direction.

As described thus far, the telescoping leaf springs have been straight and the degree of biasing adjusted by rotating their attachment using the drive unit. In other embodiments, biasing can be adjusted by selecting from a kit, inventory or collection of bent or otherwise pre-biased telescoping leaf springs or other elastin coupling members. In that way, the biasing force can be varied by selecting a spring with a desired shape and spring force instead of adjusting a drive unit to orient a straight spring element. In still other embodiments, the drive units described herein could be used to further bias a bent or other pre-biased spring element.

In specific embodiments, the axially extendable leaf springs comprise a pair of spring plates slidably secure to each other where an inferior end of a first in the plates is pivotably attached to the horizontal biasing member and a superior end of a second of the plates is secured to the universal joint. The horizontal biasing member typically comprises a rotatable axle attached to an inferior end of the first of the plates and a clamp to fix the extendable leaf spring at a selected deflection relative to the horizontal axis. The universal joint typically comprises a ball fixed to a superior end of the second plate and a socket fixed to the superior ring structure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While this invention may be embodied in many different forms, the following descriptions and drawings describe in detail specific embodiments thereof with the understanding that the present disclosure is to be considered as an exemplification of the principles of the invention and is not to be limited to the specific embodiments described.

Figure 4:
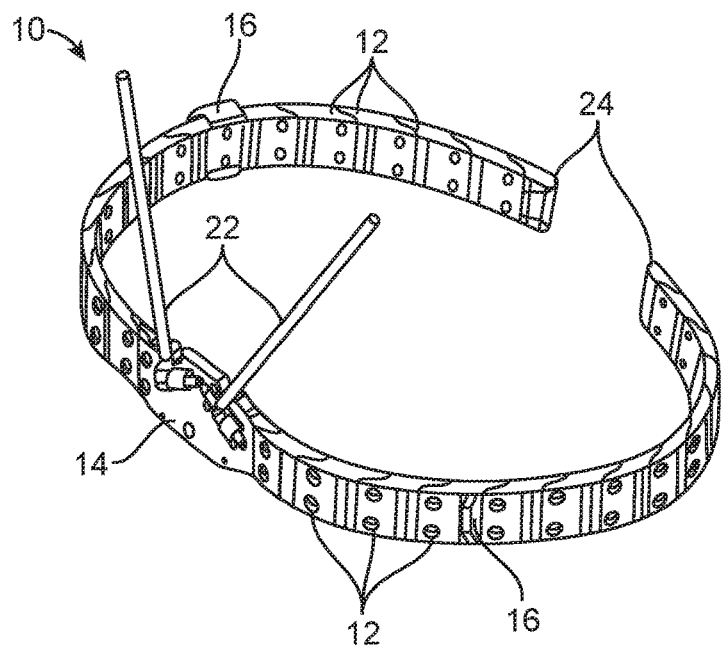
FIGS. 4 and 5 illustrate an exemplary a modular ring structure comprising a plurality of individual ring elements that can be secured together in patterns selected to conform to different patient anatomies.
Figure 5:
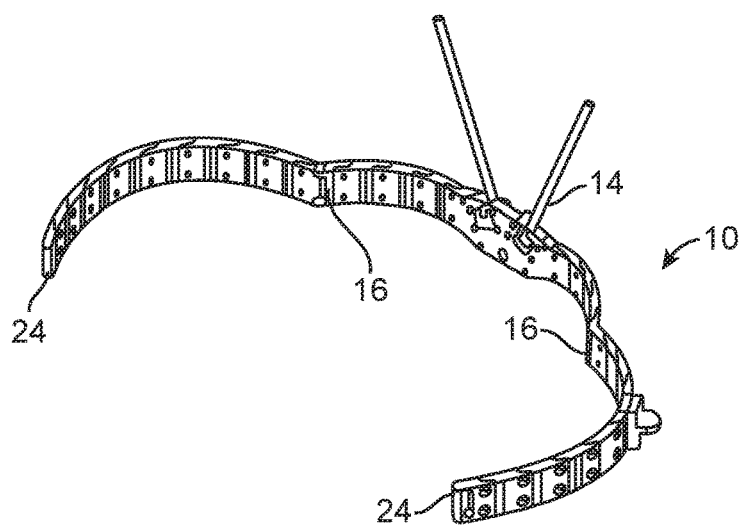
Figure 6:
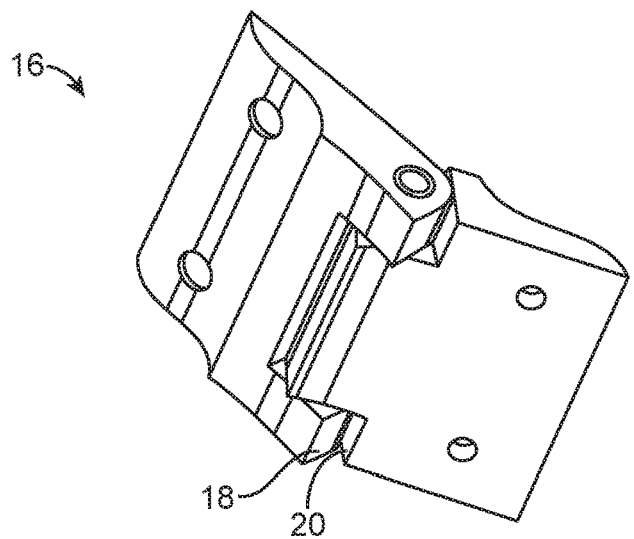
FIG. 6 illustrates a hinged ring element intended to secure a drive unit or receiver unit into the modular ring structures of the present invention.

As shown in FIG. 4, an embodiment of a ring structure 10 for incorporation into orthoses for the correction of spinal deformity comprises a plurality of ring elements joined in a manner as will be described below. The ring structure includes a posterior drive element 14 along its posterior side and a pair of hinge elements 16 which allow the ring structure to be open, as shown in FIG. 5. The hinge element 16 are shown in detail in FIG. 6 and include a pair of stop surfaces 18 and 20 which allow the ring structure to open but which engage each other and provide width for a rigid closure when the ring structure is in the closed configuration as shown in FIG. 4. The posterior drive unit includes a pair of coupling members 22 which are joined to receiver elements on a vertically adjacent ring element, as will be described in more detail below.

Figure 7A:
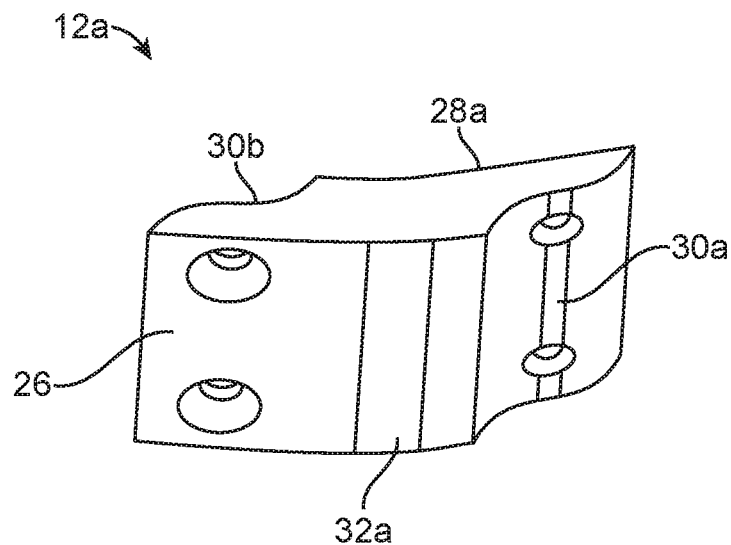
FIGS. 7A and 7B illustrate a pair of individual ring elements having different shapes.
Figure 7B:
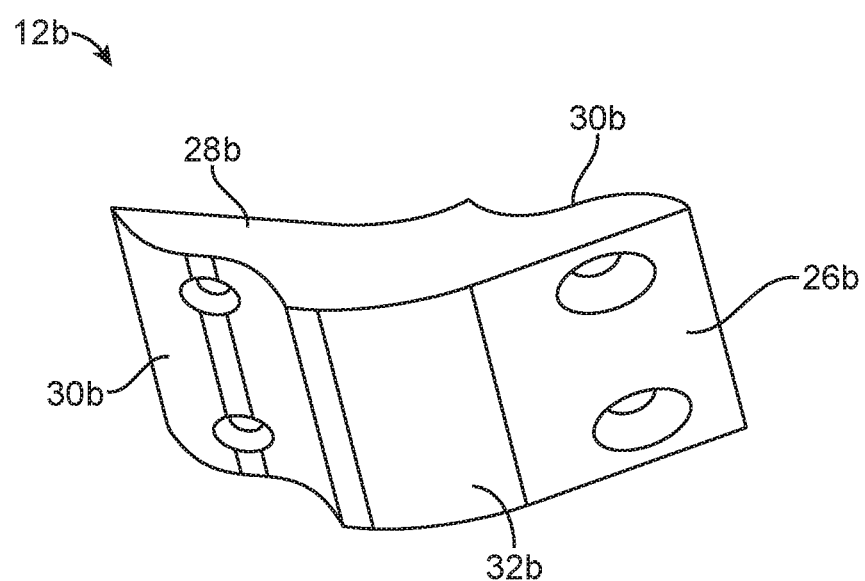

Individual ring elements 12 available for assembly into the ring structures will have similar but not identical constructions. Referring in particular to FIG. 7A, an exemplary ring element 12a includes an exterior surface 26a, an interior surface 28a, and a pair of mating surfaces 30a. The mating surfaces 30 are joined together by a curved center region 32a, and it is the length and degree of curvature of the curved region 32a which typically distinguishes among different ring elements. For example, as shown in FIG. 7B, the ring element 12b can have similar mating areas 30A and 30B but can have a curved center regions 32b which has a greater degree of curvature and a different length than that curved region 32a of ring element 12a. By having an inventory of such ring elements with varying degrees of curvature and length, a virtually unlimited number of specific ring structure geometries can be assembled. In the embodiments of FIGS. 7A and 7B, adjacent ring elements 12 will be joined by the enclosure of other threaded fasteners inserted into holes in the mating surfaces. In this way, a high degree of rigidity between adjacent individual ring elements 12 may be achieved.

Figure 8A:
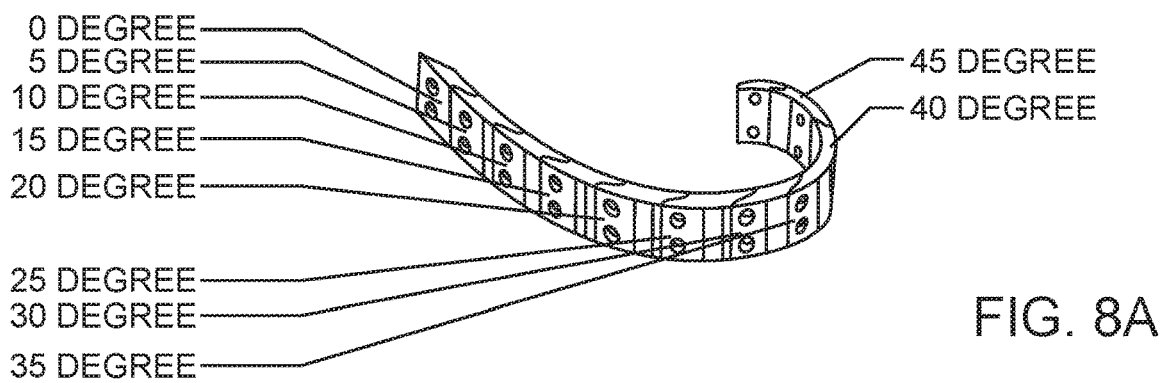
FIG. 8A-8D illustrate different degrees of curvature that can be achieved by joining individual ring elements having different shapes
Figure 8B:
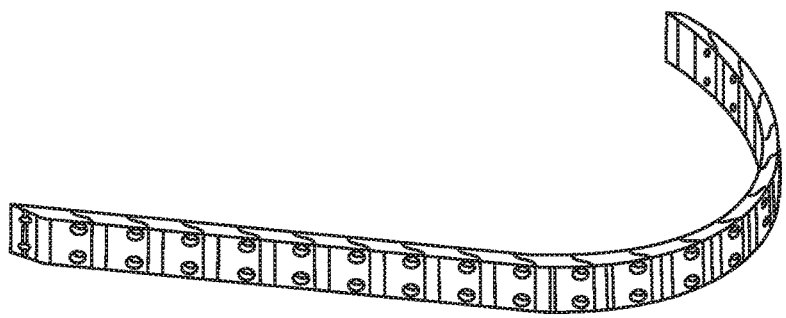
Figure 8C:
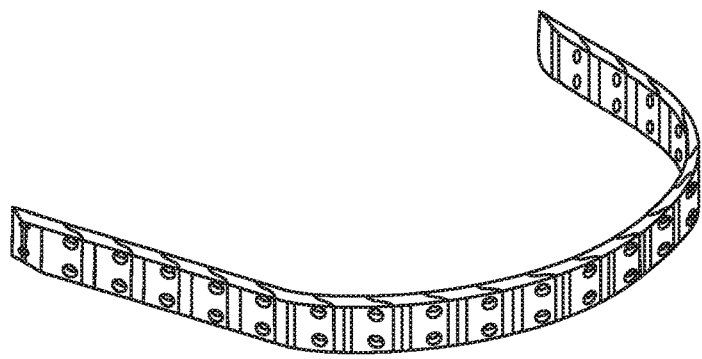
Figure 8D:
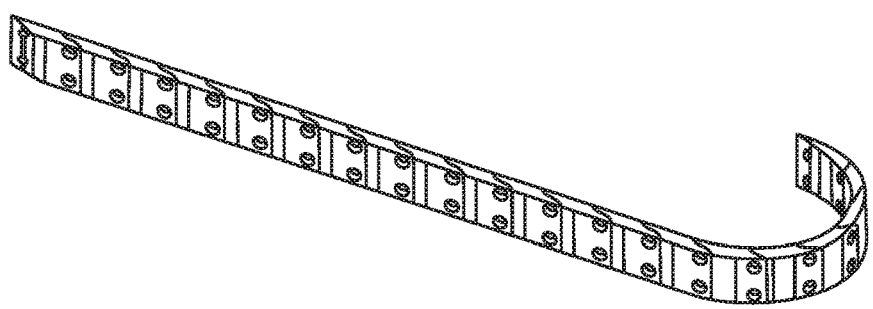

FIGS. 8A through 8D illustrate how different degrees of curvature that can be achieved by utilizing ring elements 12 having different curvatures. FIG. 8A shows how different degrees of curvature will provide much tighter curves in a ring structures. FIGS. 8B-8D are examples of curves that can be achieved once the individual ring elements are attached to each other.

Figure 9:
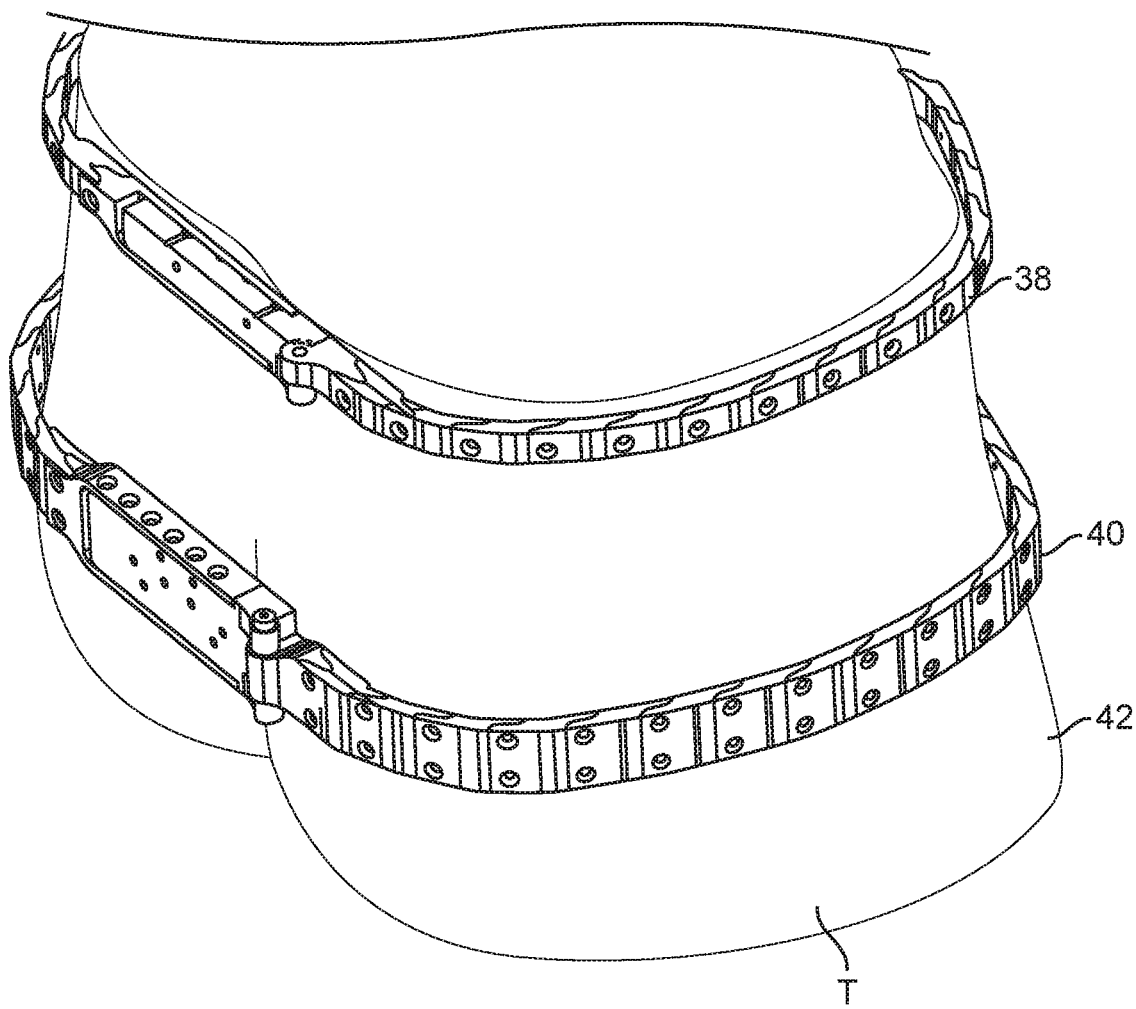
FIG. 9 illustrates a pair of exemplary ring structures mounted on a soft cover surrounding a patient's torso.

Referring now to FIG. 9, a pair of exemplary ring structures 38 and 40 are shown mounted on a soft cover 42 for positioning the ring structures on a torso T. It can be seen that the width of this ring structure may vary in an individual orthosis. It is to be noted that no coupling elements or drive units are shown between the vertically adjacent ring structures 38 and 40 but typically those would be provided.

Figure 1:
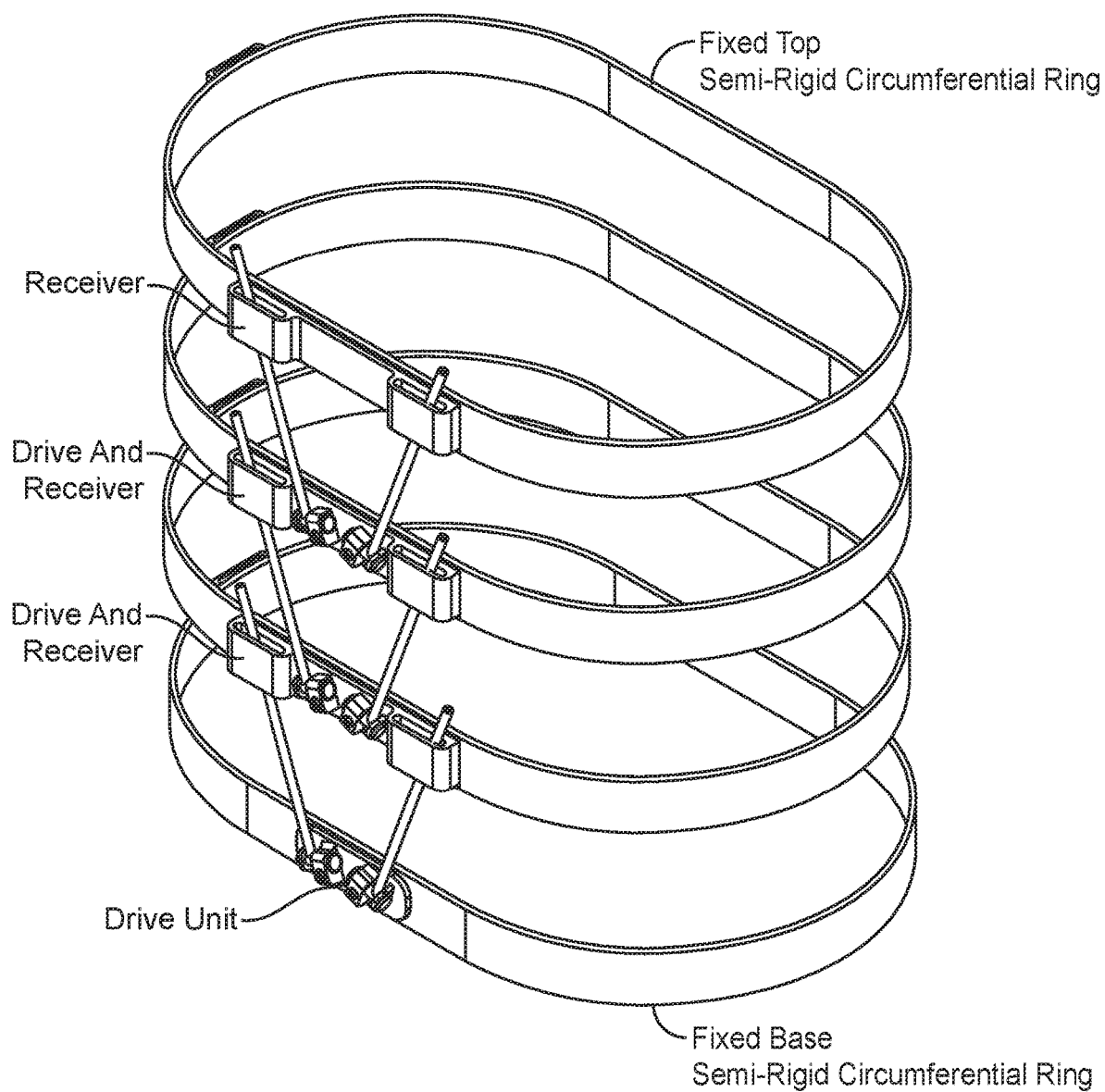
FIGS. 1, 2A-2C and 3 illustrate features of the orthosis of U.S. Patent Publication 2015/0297387.
Figure 2:
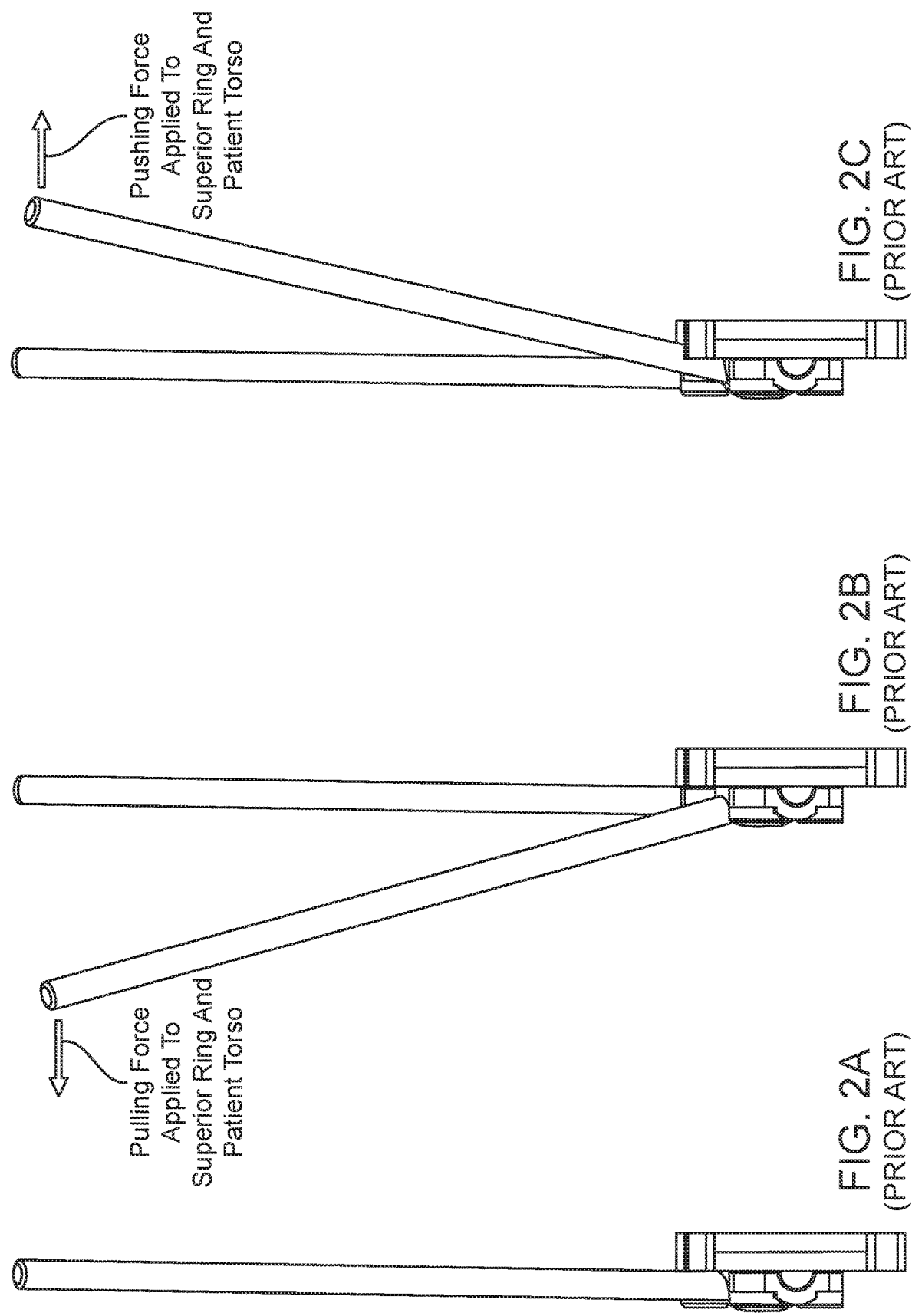
Figure 3:
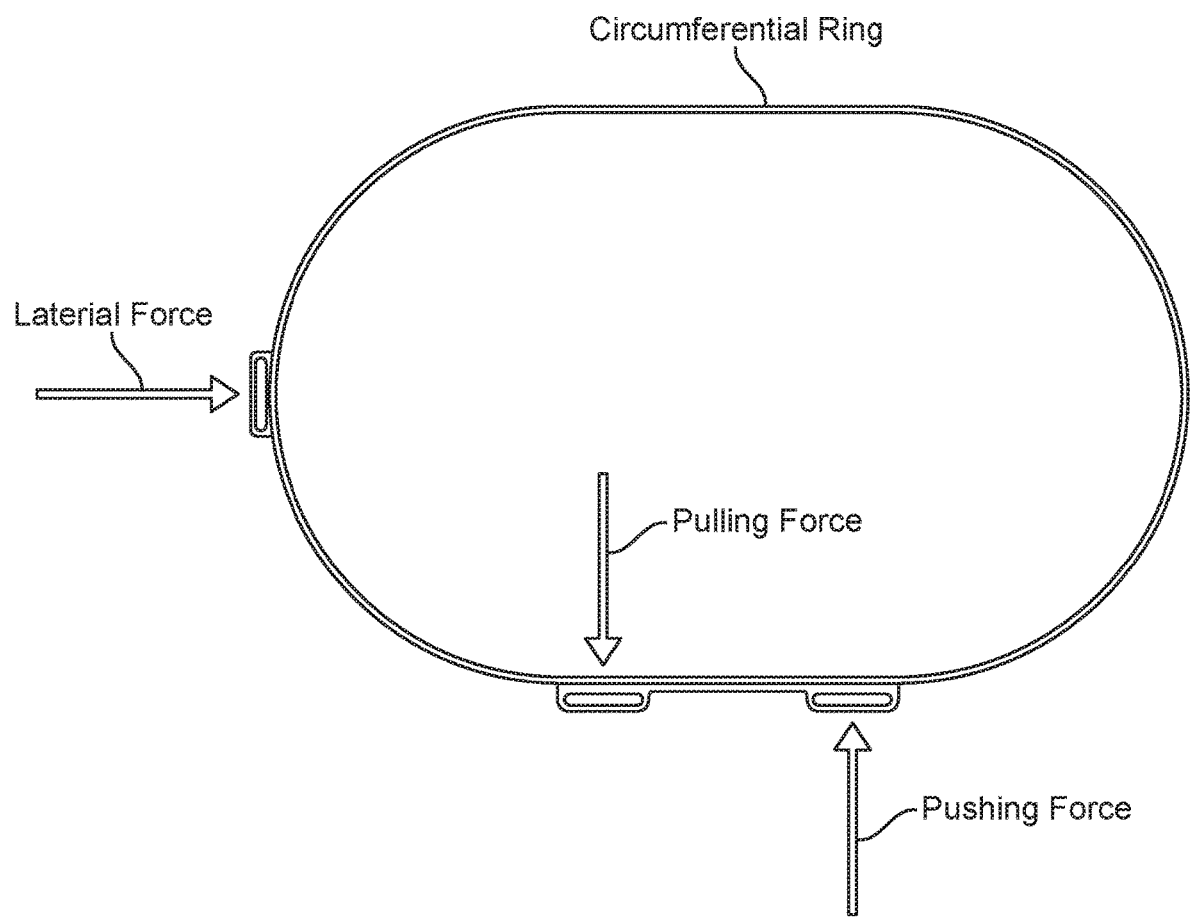
Figure 10:
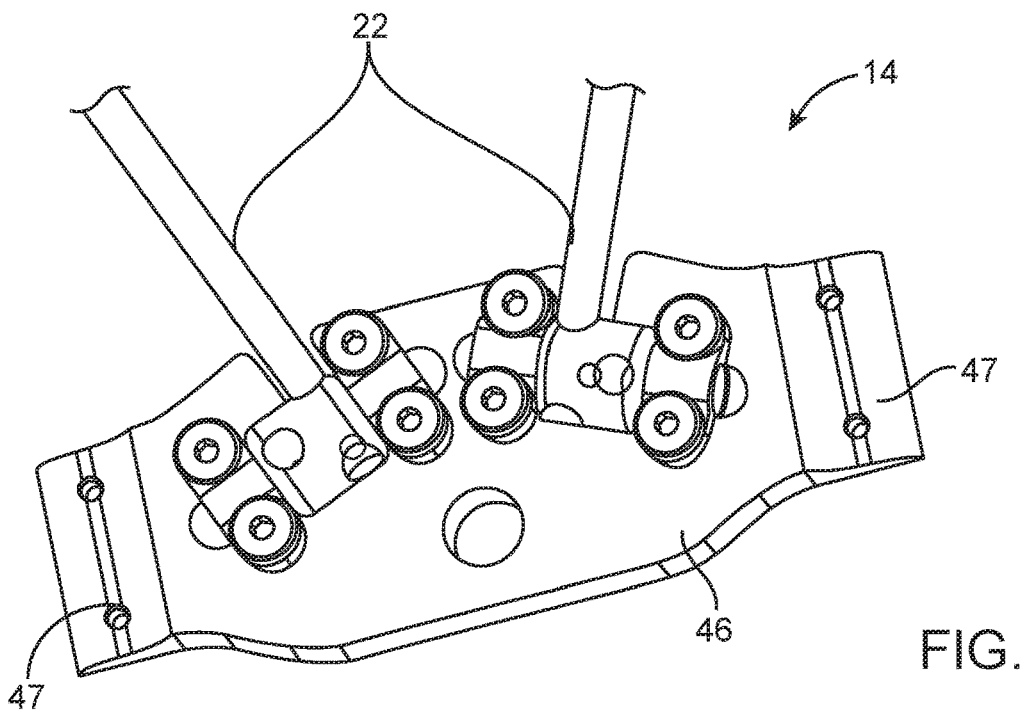
FIG. 10 illustrates an exemplary posterior drive unit.
Figure 11:
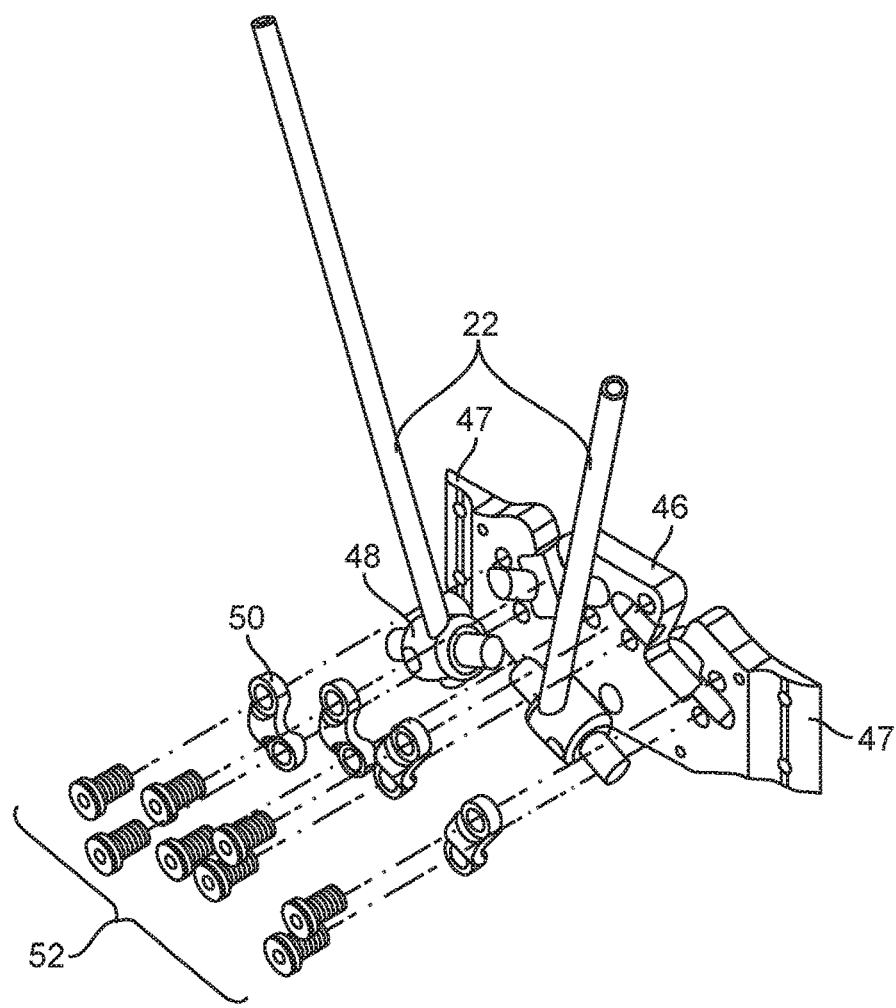
FIG. 11 is an exploded view of the exemplary posterior drive unit of FIG. 9.

Referring now to FIGS. 10 and 11, the posterior drive unit 14 illustrated previously will be described in more detail. The posterior drive unit 14 includes a base plate 46 having mating surfaces 47 at either end so that the base unit can be rigidly connected to adjacent ring elements 12 within a ring structure 10. The coupling members 22 are secured at their lower or inferior ends to cylindrical axles 48. Each axle, in turn, is secured to the base plate 46 by a saddle 50, and the saddles 50 may be tightened over the axles 48 by set screws 52. In this way, the coupling members 22 may be selectably positioned or deflected relative to the plane of the base plate 46 so that they can be oriented horizontally inwardly or outwardly, as shown in prior art FIGS. 2B and 2C. The coupling members 22 are elastic and, in this way, can provide biasing forces to a vertically adjacent ring structure as has been described previously.

Figure 12:
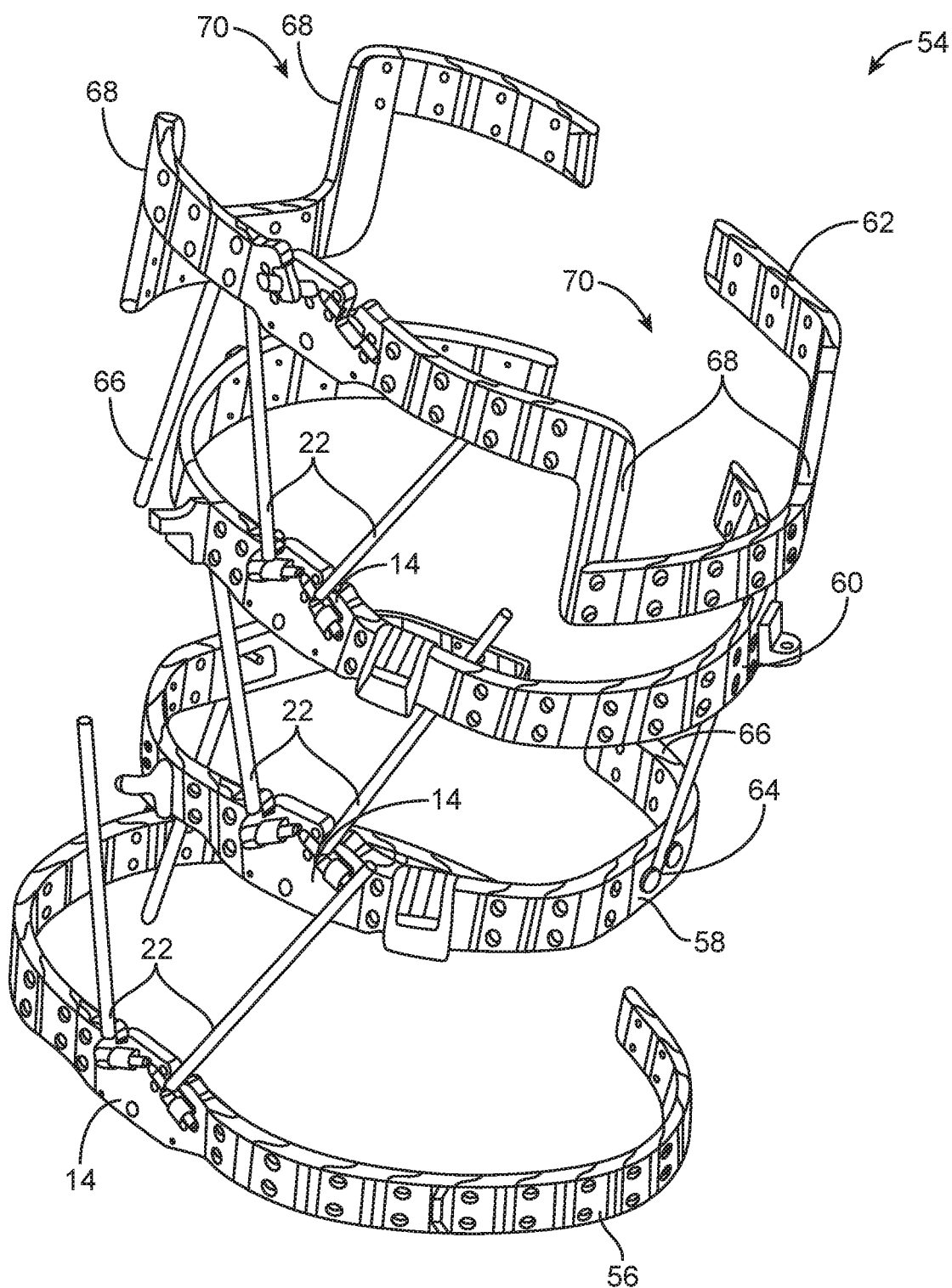
FIG. 12 illustrates a four-level orthosis constructed in accordance with the principles of the present invention having a superior ring structure adapted to conform to a patient's shoulders.
Figure 13:
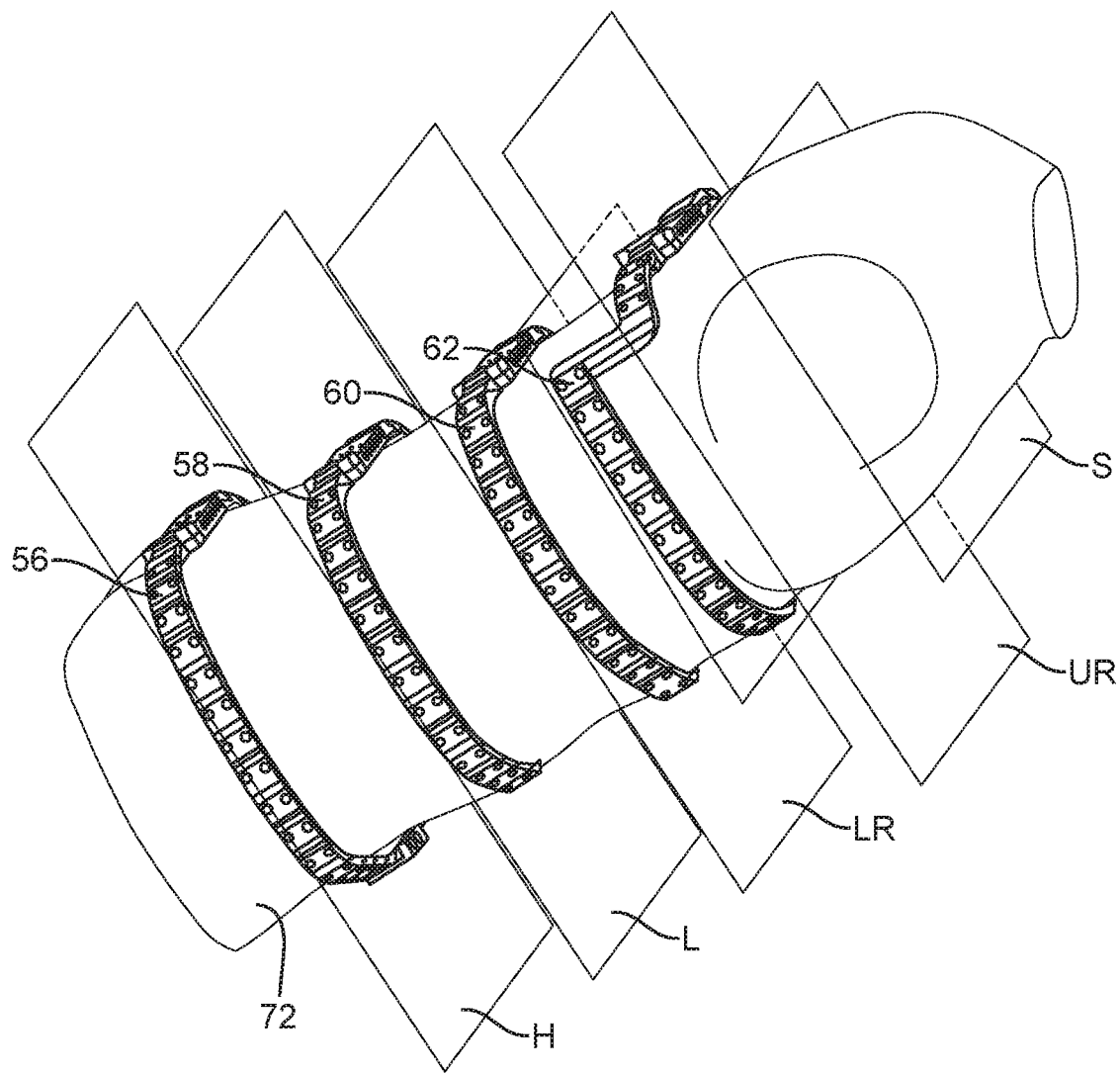
FIG. 13 illustrates the anatomical levels or planes which are engaged by an orthosis similar as is illustrated in FIG. 12, with the rings matted on a soft cover.
Figure 14:
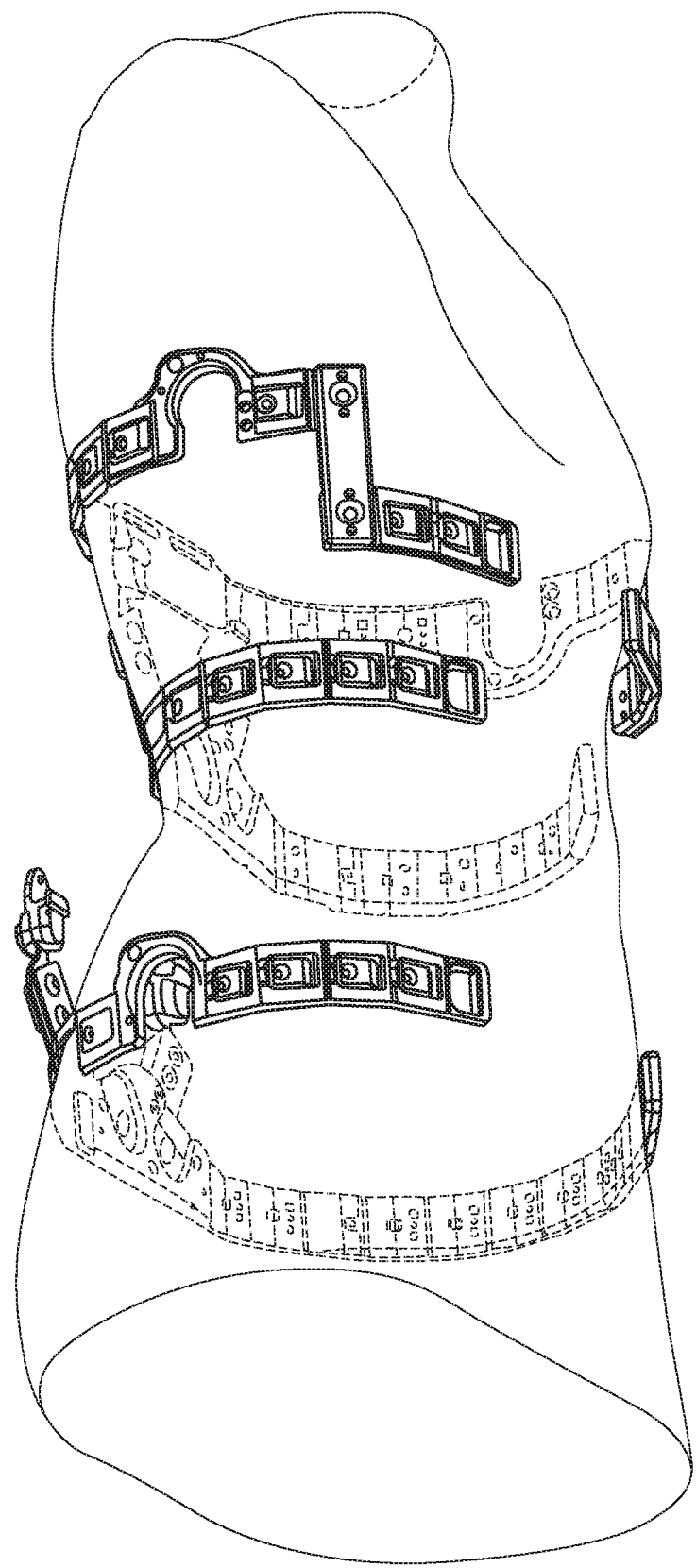
FIG. 14 is another illustration of the orthosis similar to that of FIGS. 12 and 13 positioned on the torso of a patient.

FIG. 12 illustrates an exemplary four-level orthosis 54 constructed in accordance within the principles of the present invention. The orthosis 54 includes a hip ring structure 56, a lumbar ring structure 58, a rib ring structure 60, and a shoulder ring structure 62. Posterior drive units 14 having coupling elements 22 are positioned between the vertically adjacent ring structures, and lateral drive units 64 having lateral coupling members 66 are provided between at least some of the adjacent ring structures. The shoulder ring structure 62 is particularly adapted for treating a patient's upper torso and includes vertical ring elements 68 which are joined to form shoulder slots 70 in the ring structure 62. The relationship between the shoulder slots 70 and a patient's torso can be seen schematically in FIGS. 13 and 14. FIG. 13 further illustrates placement of the orthosis on a soft cover 72 where the hip ring structure 56 engages the patient at a hip level H, the lumbar ring structure 58 engages the patient at a lumbar level L, the rib ring structure 16 engages the patient's lower rib LR, and the shoulder ring structure engages the patient's upper ribs UR and shoulder level S. The ring structures 56, 58, 60, and 62 are secured to soft cover 72 to maintain the rings at their desired levels when the soft cover is worn by the patient.

Figure 15A:
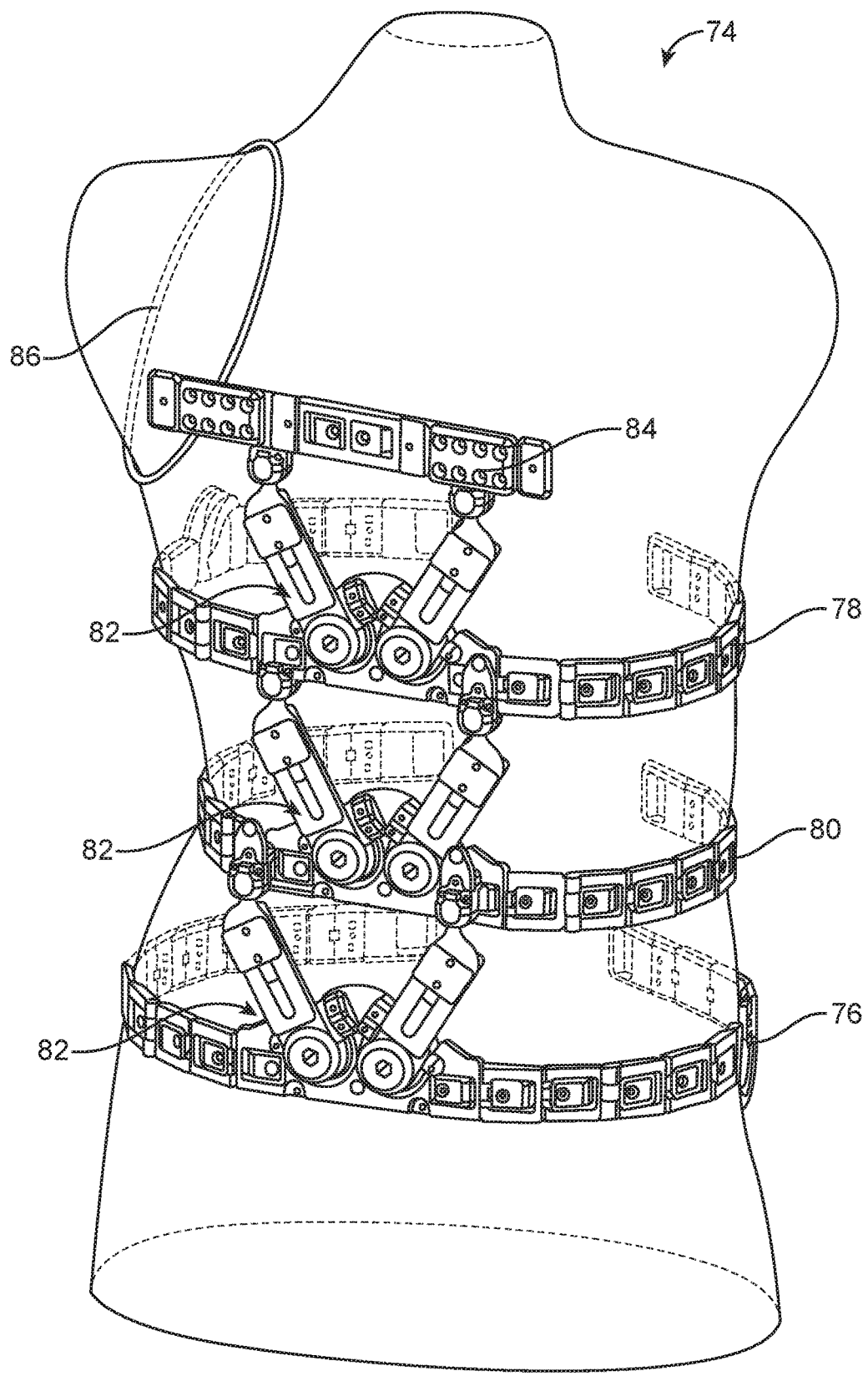
FIGS. 15A and 15B illustrates an alternative orthosis structure having a posterior plate at its superior end with a shouldering adapted to apply forces from the posterior to the patient's shoulder.
Figure 15B:
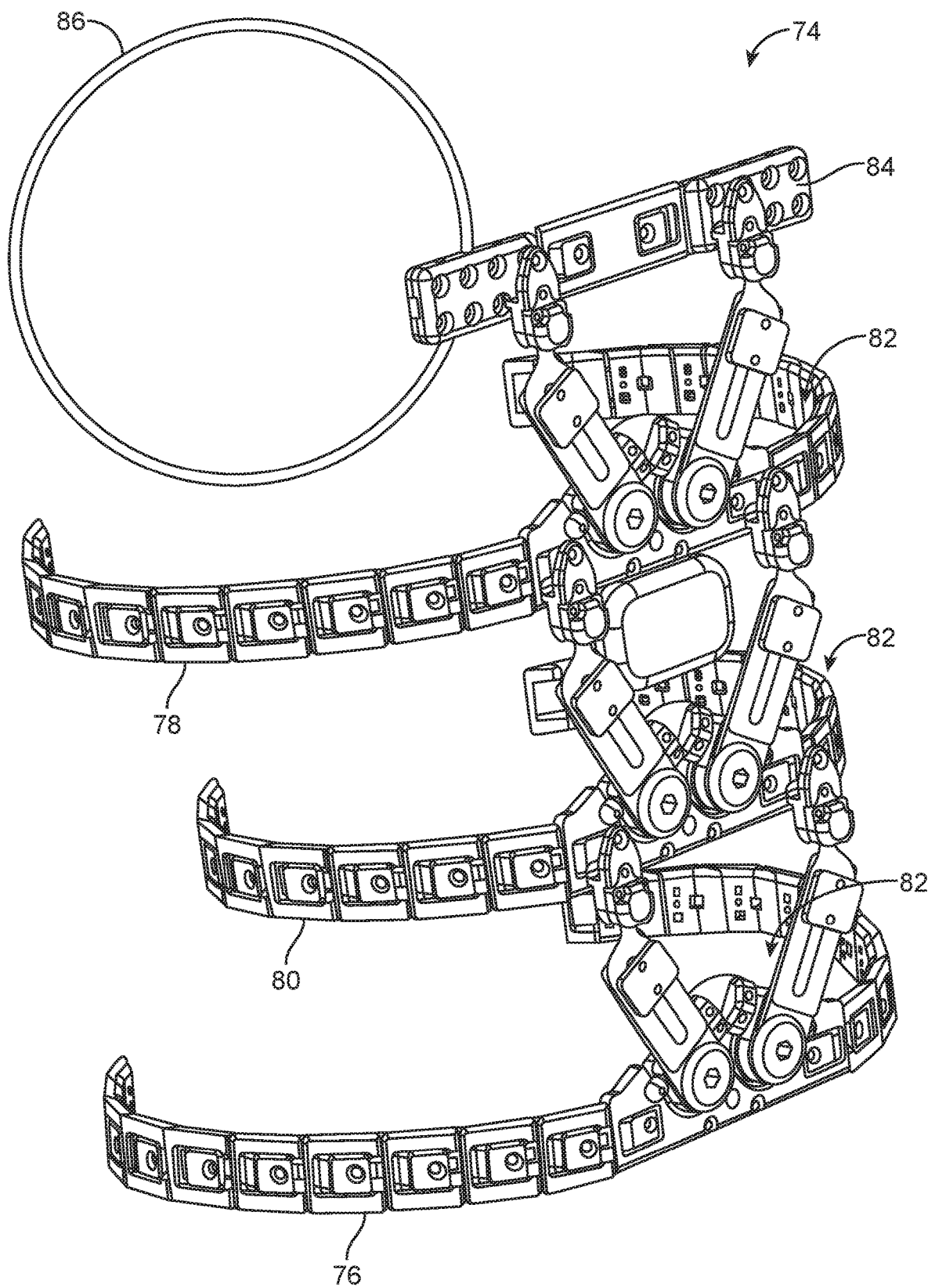

Referring now to FIGS. 15A and 15B, another orthosis 74 constructed in accordance with the principles of the present invention will be described. The orthosis 74 includes an inferior ring structure 76, a superior ring structure 78, and a single intermediate ring structure AD. The ring structures are joined by posterior drive units 82 and an uppermost of the drive units is attached at its upper ends to an upper plate 84. The plate 84, unlike the ring structures, does not circumscribe the patient, but instead is attached at one end to a shoulder ring 86 in order to apply corrective forces to one of the patient's shoulders. In particular, the posterior drive unit 82 can be biased to pull or push the ring 86 and thus the shoulder in a desired direction. Although illustrated as a wire ring, the shouldering 86 can have a variety of structures including straps, belts, and the like.

Figure 16:
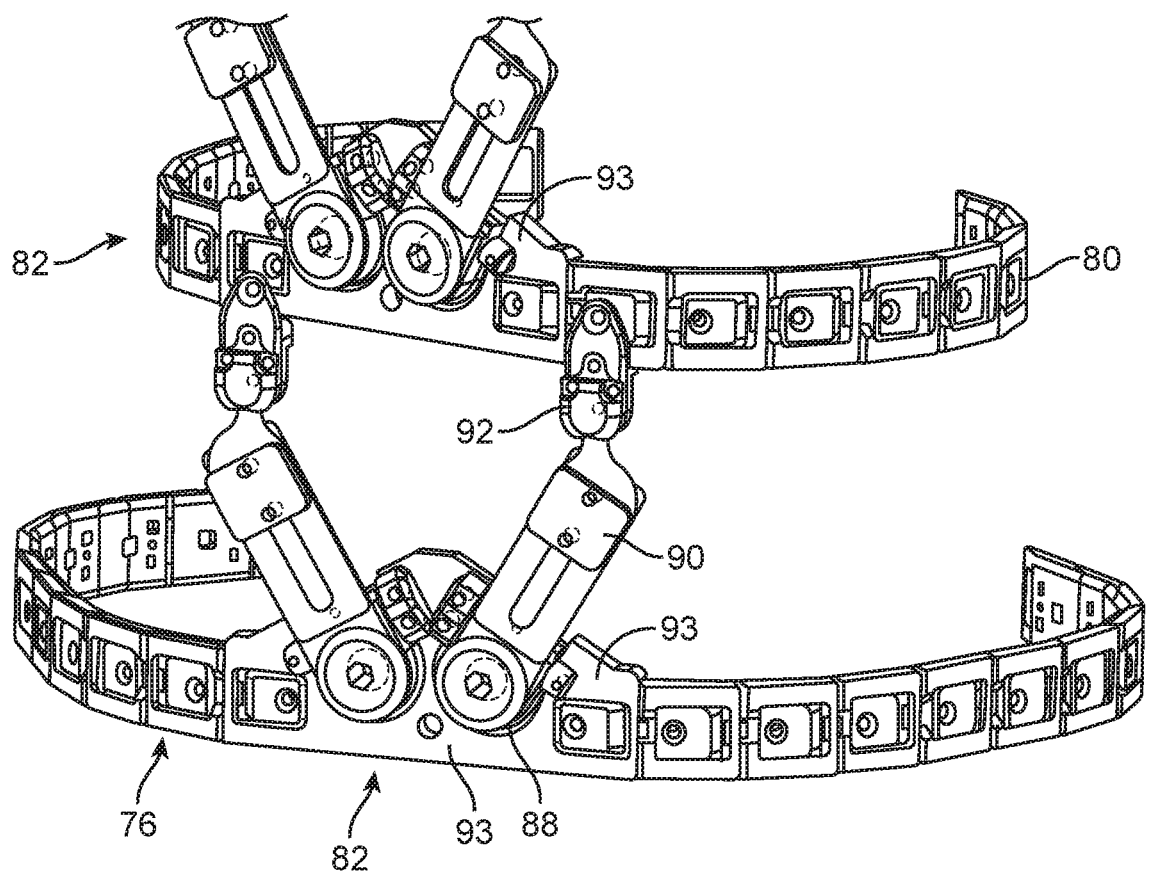
FIG. 16 illustrates the lower rings of the orthosis of FIGS. 15A and 15B, illustrating a specific embodiment of posterior drive unites.
Figure 20:
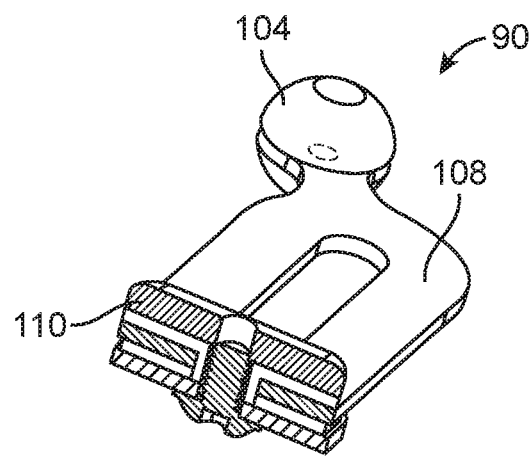

Referring now to FIGS. 16 to FIGS. 16-20, the posterior drive units 82 of orthosis of the ball will be described in more detail. Each posterior drive unit 82 includes a telescoping leaf spring 90 which is joined at its lower end to the lower the inferior ring structure 76 by a bolt 88 and at its upper end to the interior ring structure 80 by a ball joint 92. The drive units 82 are attached to their respective ring structures by base plates 93.

Figure 17:
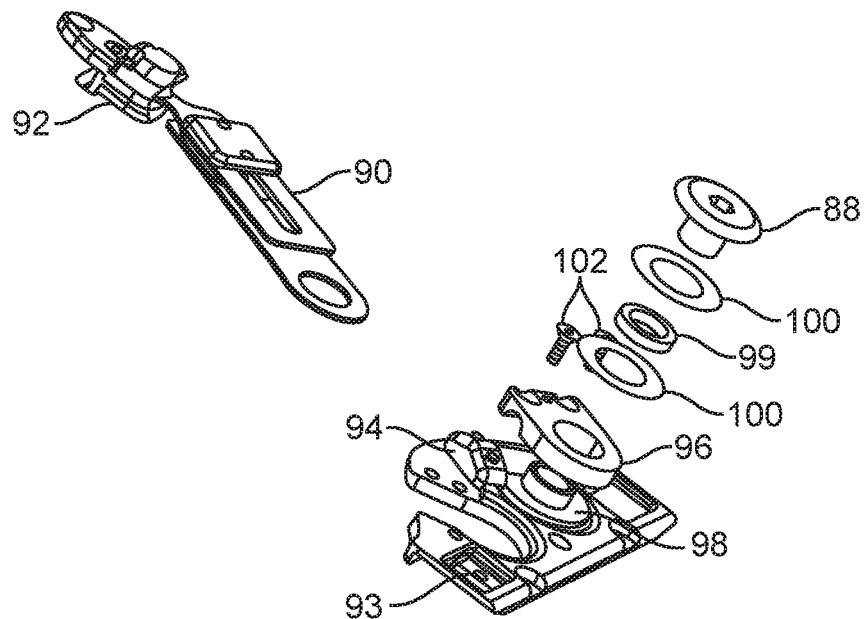
FIG. 17 is an exploded view of the posterior drive unit of FIG. 16.

As shown in particular in FIG. 17, the telescoping leaf spring 90 is secured to an axle 94 and held in place by a top clamp 96 and a bottom clamp 98. The top clamp 96 and bottom clamp 98, in turn, are compressed by an assembly including bolt 88, spacer 99, and a pair of washers 100. The top clamp 96 and bottom clamp 98 can be tightened together by set screws 102. In this way, the telescoping leaf spring 90 can be manually placed at a desired degree of deflection (to achieve a desired biasing force) and that deflection set by tightening the top clamp over the bottom clamp using the set screws and tightening the bolt 88. By having a spacer 99 thicker than the leaf spring 90 rotation of the leaf spring about the axis of the bolt 88 is allowed, enhancing patient range of motion.

Figure 18:
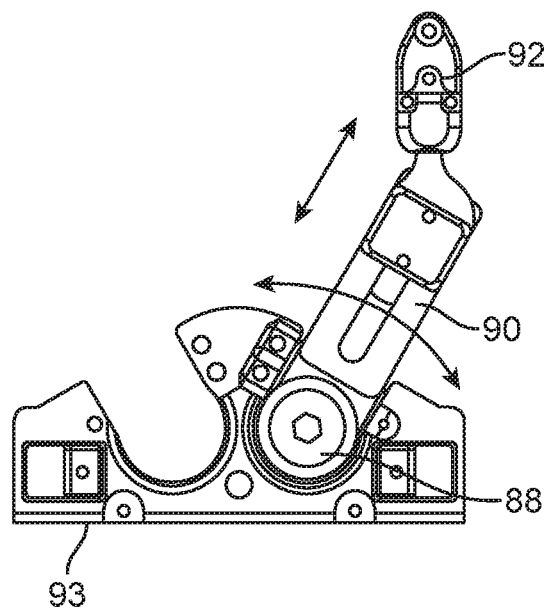
FIG. 18 illustrates the freedom of motion of the posterior drive unit of FIGS. 16 and 17.

The presence of the spacer 99 and washers 100, however, allows the telescoping leaf spring 90 to pivot to accommodate patient movement as shown by the arrow in FIG. 18. In addition, the telescoping leaf spring 90 is able to axially extend and retract as shown by a second arrow in FIG. 18 to further accommodate patient motion. The leaf spring 90 will be fixed in the anterior-posterior direction to apply a relatively constant force to the patient while being able to move in other directions to accommodate patient movement. Patient movement is further accommodated by the universal joint 92 which secures the superior end of the leaf spring to the upper ring structure.

Figure 19:
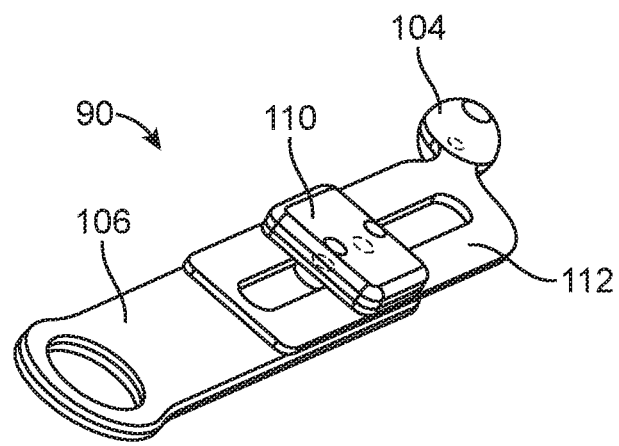
FIGS. 19 and 20 illustrate the components of the telescoping leaf spring of the posterior drive unit of FIGS. 16-18.

Referring now to FIGS. 19 and 20, the telescoping leaf spring 90 comprises an inner plate 106, an outer plate 108, and a retainer 110 which joins the plates together and allows them to slide in slot 112. Ball 104 attached to the outer plate 108 is received in the ball joint 82.

Figure 21:
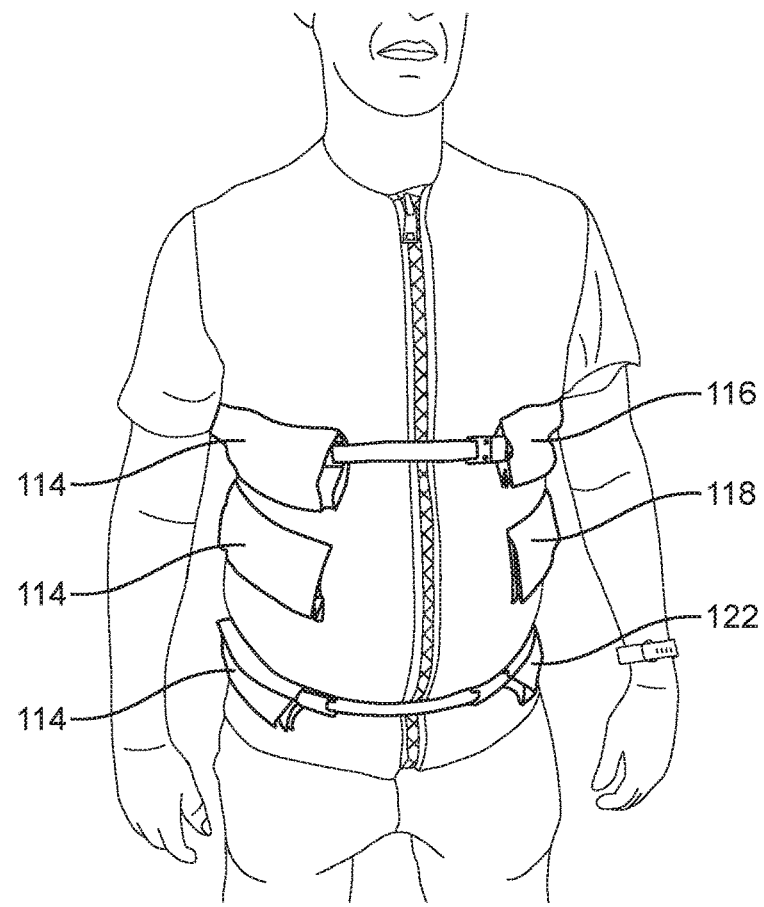
FIGS. 21 and 22 illustrate a soft cover having pockets or pouches for securing the rings structures of the present invention to a patient.
Figure 22:
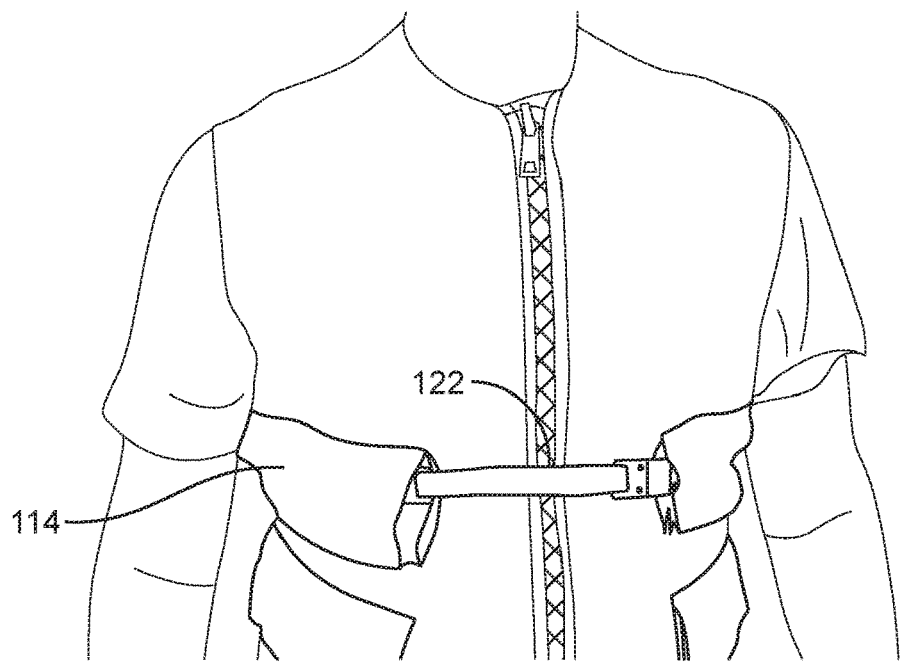

Referring now to FIGS. 21 and 22, a soft cover 116 for supporting the orthosis of the present invention is illustrated. Soft cover 116 comprises a vest or similar garment, typically having a zipper or other closure on its front face. In addition, the soft cover will typically include a plurality of pouches or receptacles 114 formed or attached at different levels along the length of the cover with the pouches configured to receive and old individual ring structures of the orthosis. In addition, straps 122 are provided to close the ring structures after they have been inserted into the pouches.

Figure 23:
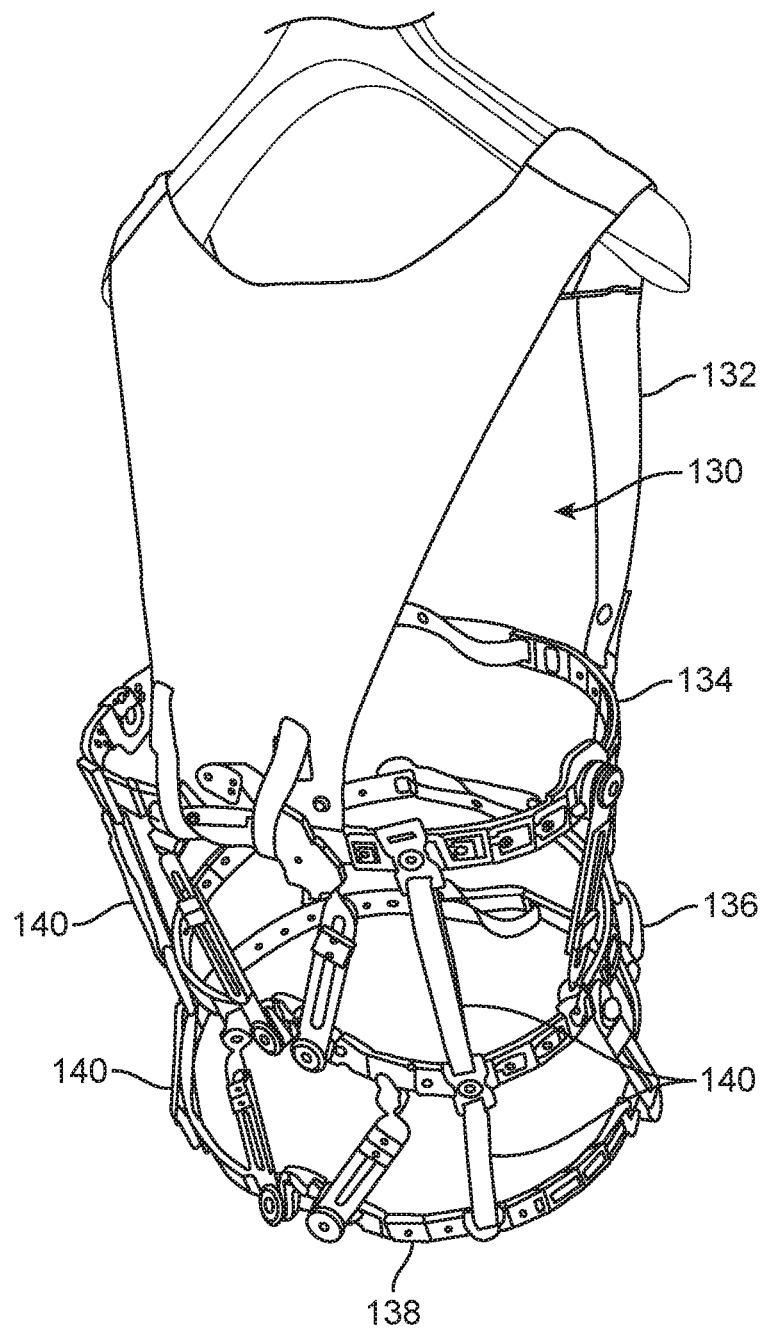
FIG. 23 illustrates an alternative rest and strap assembly for suspending the orthosis of the present invention on the patient.

Referring now to FIG. 23, an alternative support assembly 130 for suspending an orthosis of the present invention on a patient is illustrated. The support assembly 130 includes a shoulder strap structure 132, illustrated as a vest having a back panel and a pair of front straps. The shoulder strap assembly 132 has Velcro® hook and loop or other similar fasteners at its lower end for attaching to the superior ring structure 134. In addition, connecting straps 140 are provided between an upper ring structure 134 and a middle ring structure 136 as well as between the middle ring structure and a lower ring structure 138 so that the ring structures of the orthosis are fully supported by the shoulder strap assembly 132. It will be appreciated that posterior and lateral drive units will also be positioned between the vertically adjacent ring structures. By supporting the ring structures with the shoulder strap assembly and lower connecting straps 140, the positions of the ring structures can be maintained while allowing flexibility and freedom of movement in the posterior and lateral drive units.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for externally applying corrective force to a torso of a patient, the system comprising:

a plurality of ring structures spaced-apart along a vertical axis, wherein the plurality of ring structures include an inferior terminal ring structure, a superior terminal ring structure, and at least one intermediate ring structure disposed between the inferior and superior terminal ring structures and wherein at least some of the plurality of ring structures comprise a plurality of ring elements, wherein at least some of the plurality of ring elements have mating surfaces disposed on lateral ends of a curved center region, wherein the mating surfaces on circumferentially adjacent ring elements have complementary shapes that allow them to be linked together so that the at least some of the ring structures conform to a circumference of the torso of the patient and wherein at least some mating surfaces are configured to rigidly attach to a circumferentially adjacent mating surface to form a selectively rigid assembly; and at least one coupling member disposed between each vertically adjacent pair of the plurality of ring structures, wherein each of the at least one coupling member is adjustably fixated at an inferior end to a ring structure located on an inferior side thereof and at a superior end to a ring structure located on a superior side thereof.

2. The system of claim 1, wherein the plurality of ring elements are configured so that individual ring elements may be added to or removed from a ring structure of the at least some of the ring structures to change at least one of a preselected size and a preselected shape of the ring structure.

3. The system of claim 2, wherein at least some of the plurality of ring elements have different geometries whereby the individual ring elements can be connected in an order selected to provide a particular peripheral shape.

4. The system of claim 1, wherein the at least some of the mating surfaces on the circumferentially adjacent ring elements are connected by threaded fasteners.

5. The system of claim 1, wherein at least some of the plurality of ring structures have anterior gaps configured to be joined by an adjustable closure component.

6. The system of claim 5, wherein the adjustable closure component comprises a strap.

7. The system of claim 1, wherein at least one coupling member disposed between vertically adjacent pairs of ring structures is located on a dorsal side of the vertically adjacent pairs of ring structures.

8. The system of claim 7, further comprising at least one additional coupling member disposed between vertically adjacent pairs of ring structures located on a lateral side of the ring structures.

9. The system of claim 1, wherein at least some of the plurality of ring structures define a periphery lying in a single plane.

10. The system of claim 9, wherein the at least some of the ring structures include linked elements which extend vertically between a first plane and a second plane.

11. The system of claim 9, wherein the superior terminal ring structure defines a periphery having portions lying in different vertically space-apart planes and all other ring structures define a periphery lying in a single plane.

12. The system of claim 1, wherein at least some of the plurality of ring structures define a periphery having portions lying in different vertically spaced-apart planes.

13. A system for externally applying corrective force to a torso of a patient comprising:
a plurality of ring structures that are each configured to conform to a circumference of the torso of the patient and are each positioned in a spaced, substantially coaxial configuration about a vertical axis, wherein the plurality of ring structures includes an inferior terminal ring structure, a superior terminal ring structure, and at least one intermediate ring structure disposed between the inferior and superior terminal ring structures and wherein the superior terminal ring structure has a length that is configured to span an upper region of the patient's back and to extend downward to span the patient's torso below the patient's arms and wherein at least some of the plurality of ring structures comprise a plurality of ring elements linked together so that the at least some of the ring structures conform to the circumference of the torso of the patient and wherein at least some of the plurality of ring elements are configured to rigidly attach to an adjacent ring element to form a rigid assembly; and at least one elastic member disposed between each vertically adjacent pair of the plurality of ring structures, wherein each of the at least one elastic member is secured and adjustably fixated at an inferior end to a ring structure located on an inferior side thereof and at a superior end to a ring structure located on a superior side thereof.

14. The system of claim 13, wherein the superior terminal ring structure is further configured to span an anterior region of the patient's torso above the patient's arms.

15. The system of claim 14, wherein the superior terminal ring structure has a posterior region, a pair of lateral regions, and an anterior region, wherein each of the posterior, lateral, and anterior regions are aligned generally horizontally relative to the vertical axis and the regions are interconnected by vertical regions.

16. The system of claim 15, wherein at least some of the plurality of ring structures comprise a plurality of elements linked together so that the at least some of the ring structures conform to the circumference of the torso of the patient.

17. The system of claim 16, wherein the plurality of elements linked together comprise both horizontal elements and vertical elements.

18. A method for configuring a system to apply a corrective force to a vertebral column of a patient, the method comprising:
providing a plurality of ring elements wherein at least some of the ring elements have mating surfaces disposed on lateral ends of a curved center region, wherein the mating surfaces on circumferentially adjacent ring elements have complementary shapes;
linking the complementary mating surfaces of individual ring elements rigidly together to form an inferior terminal ring structure, a superior terminal ring structure, and at least one intermediate ring structure disposed between the inferior and superior terminal ring structures, wherein each ring structure conforms to a circumference of a torso of the patient and wherein at least some individual ring elements are selectively rigidly attached to an adjacent ring element; and
elastically joining the inferior terminal ring structure, the superior terminal ring structure, and the at least one intermediate ring structure along a vertical axis to form the system.

19. The method as in claim 18, wherein at least some of the individual ring elements have different geometries.

20. The method as in claim 19, wherein at least 50% of the individual ring elements have different geometries.

21. The method as in claim 18, wherein elastically joining the inferior terminal ring structure, the superior terminal ring structure, and the at least one intermediate ring structure along a vertical axis comprises placing at least one elastic coupling member between each vertically adjacent pair of ring structures.

22. The method as in claim 21, wherein each elastic coupling member is secured and adjustably fixated at an inferior end to an inferiorly adjacent ring structure and at a superior end to a superiorly adjacent ring structure.

23. The method as in claim 18, wherein rigidly mating the at least some of the ring elements having mating surfaces on circumferentially adjacent ring elements comprises using threaded fasteners.

* * * * *